(12) United States Patent
Tschirschwitz et al.

(10) Patent No.: US 10,815,168 B2
(45) Date of Patent: Oct. 27, 2020

(54) CHEMICAL CONVERSION PROCESS IN A DISPERSION

(71) Applicant: BASF SE, Ludwigshafen (DE)

(72) Inventors: Steffen Tschirschwitz, Mannheim (DE); Joni Joni, Sulzbach (DE); Jochen Bürkle, Mannheim (DE); Stefan Bitterlich, Dirmstein (DE); Daniel Pfeiffer, Neustadt (DE); Michael Hübner, Lampertheim (DE); Nicole Holub, Mannheim (DE)

(73) Assignee: BASF SE (DE)

(*) Notice: Subject to any disclaimer, the term of this patent is extended or adjusted under 35 U.S.C. 154(b) by 197 days.

(21) Appl. No.: 13/937,351

(22) Filed: Jul. 9, 2013

(65) Prior Publication Data

US 2014/0018591 A1 Jan. 16, 2014

Related U.S. Application Data

(60) Provisional application No. 61/670,130, filed on Jul. 11, 2012.

(51) Int. Cl.
*C07C 5/29* (2006.01)
*C07C 5/27* (2006.01)

(52) U.S. Cl.
CPC ............ *C07C 5/29* (2013.01); *C07C 2601/14* (2017.05)

(58) Field of Classification Search
CPC ....... C07C 5/29; C07C 2101/14; C07C 13/18; C07C 13/00; C07C 5/2721; B01J 27/06
USPC .......................................................... 585/373
See application file for complete search history.

(56) References Cited

U.S. PATENT DOCUMENTS

| | | | |
|---|---|---|---|
| 3,271,467 A | 9/1966 | Nakayama | |
| 3,406,217 A | 10/1968 | Davison et al. | |
| 5,824,832 A * | 10/1998 | Sherif | B01J 31/0278 556/138 |
| 6,503,465 B1 | 1/2003 | Lin et al. | |
| 2003/0060359 A1 * | 3/2003 | Olivier-Bourbigou | B01J 31/0225 502/150 |
| 2003/0109767 A1 | 6/2003 | Vasina et al. | |
| 2010/0130800 A1 * | 5/2010 | Luo et al. | 585/446 |
| 2011/0137097 A1 | 6/2011 | Tschirschwitz et al. | |

(Continued)

FOREIGN PATENT DOCUMENTS

EP 1 310 472 A1 5/2003
EP 1503236 A1 2/2005

(Continued)

OTHER PUBLICATIONS

Haynes, W. M. "CRC Handbook of Chemistry and Physics", Internet Version 2015, Section 3, p. 366.*

(Continued)

*Primary Examiner* — Youngsul Jeong
(74) *Attorney, Agent, or Firm* — Faegre Drinker Biddle & Reath LLP

(57) ABSTRACT

The present invention relates to a chemical conversion process, preferably an isomerization process, for at least one hydrocarbon in the presence of an ionic liquid. The chemical conversion is performed in a dispersion, with dispersion of the hydrocarbon (phase (B)) in the ionic liquid (phase (A)) in the dispersion, the volume ratio of phase (A) to phase (B) being in the range from 2.5 to 4:1 [vol/vol].

16 Claims, 1 Drawing Sheet

(56) References Cited

U.S. PATENT DOCUMENTS

2011/0137098 A1* 6/2011 Tschirschwitz et al. ..... 585/374
2011/0155632 A1  6/2011 Timken et al.
2011/0155640 A1* 6/2011 Timken et al. ................ 208/97

FOREIGN PATENT DOCUMENTS

| WO | WO-2010062922 A2 | 6/2010 |
| WO | WO-2010074836 A2 | 7/2010 |
| WO | WO-2010075038 A2 | 7/2010 |
| WO | WO-2011069929 A1 | 6/2011 |
| WO | WO-2011069957 A1 | 6/2011 |
| WO | WO-2012104769 A1 | 8/2012 |

OTHER PUBLICATIONS

Zhang, S.; Sun, N.; He, X.; Lu, X.; Zhang, X. "Physical Properties of Ionic Liquids: Database and Evaluation", J. Phys. Chem. Ref. Data., 2006, 35, pp. 1475-1517.*
Haynes, W.M. "CRC Handbook of Chemistry and Physics", 95th ed. Internet Version (2015); p. 366.*
Freemantle, M. "An Introduction to Ionic Liquids", RSC Publishing (Cambridge); 2010; p. 71.*
U.S. Appl. No. 61/438,686, filed Feb. 2, 2011.
U.S. Appl. No. 61/670,131, filed Jul. 11, 2012.
U.S. Appl. No. 61/670,132, filed Jul. 11, 2012.
U.S. Appl. No. 61/670,133, filed Jul. 11, 2012.
U.S. Appl. No. 61/670,134, filed Jul. 11, 2012.
U.S. Appl. No. 61/670,135, filed Jul. 11, 2012.
U.S. Appl. No. 61/670,136, filed Jul. 11, 2012.
U.S. Appl. No. 61/670,140, filed Jul. 11, 2012.
U.S. Appl. No. 61/670,142, filed Jul. 11, 2012.
Ksenofontov, V.A., et al., "Isomerization of Cyclic Hydrocarbons Mediated by an $AlCl_3$-based Ionic Liquid as Catalyst", React. Kinet. Catal. Lett., vol. 80, No. 2, (2003), pp. 329-335.
International Search Report for PCT/EP/2013/064441 dated Oct. 16, 2013.

* cited by examiner

CHEMICAL CONVERSION PROCESS IN A DISPERSION

This patent application claims the benefit of pending U.S. provisional patent application Ser. No. 61/670,130 filed on Jul. 11, 2012, incorporated in its entirety herein by reference.

The present invention relates to a chemical conversion process, preferably an isomerization process, for at least one hydrocarbon in the presence of an ionic liquid. The chemical conversion is performed in a dispersion, with dispersion of the hydrocarbon (phase (B)) in the ionic liquid (phase (A)) in the dispersion, the volume ratio of phase (A) to phase (B) being in the range from 2.5 to 4:1 [vol/vol].

Ionic liquids, especially acidic ionic liquids, are suitable, inter alia, as catalysts for the isomerization of hydrocarbons. A corresponding use of an ionic liquid is described, for example, in WO 2011/069929, where a specific selection of ionic liquids is used in the presence of an olefin for isomerization of saturated hydrocarbons, more particularly for isomerization of methylcyclopentane (MCP) to cyclohexane. In the process according to WO 2011/069929, the hydrocarbons to be isomerized and the ionic liquids can in principle be used in any ratios. In the working examples, a five-fold volume excess of ionic liquids is used. A similar process is described in WO 2011/069957, but the isomerization therein is not effected in the presence of an olefin, but with a copper(II) compound.

US-A 2003/0109767 discloses a process for isomerizing $C_5$-$C_8$ paraffin hydrocarbons (paraffins) in the presence of an ionic liquid as a catalyst. The ionic liquid comprises, as cations, nitrogen-containing heterocycles or nitrogen-containing aliphatics; the corresponding anions are derived from metal halides. The paraffins to be isomerized are linear alkanes such as n-hexane or n-octane and monosubstituted alkanes such as 3-methylhexane or mixtures thereof. The process described in US-A 2003/0109767 is intended to prepare paraffins having a relatively high degree of branching. With regard to the ratios of ionic liquid to hydrocarbon to be isomerized, there are no restrictions in principle; in the working examples, amounts in a ratio of 1:1 or a maximum 1.5-fold excess of ionic liquid are used.

In the isomerization process described in EP-A 1 503 236, the intention is likewise to obtain a relatively high degree of branching in the paraffins (hydrocarbons) to be isomerized in the presence of an ionic liquid. The isomerization process is additionally performed in the presence of cyclic hydrocarbons as additives and in a reaction medium, the cyclic hydrocarbons comprising a tertiary carbon atom as a structural unit, or being converted by the reaction medium to a corresponding compound having such a structural unit. Preference is given to using methylcyclohexane or dimethylcyclopentane as such cyclic hydrocarbon additives. The paraffins to be isomerized are linear alkanes such as n-butane or n-octane, and monomethyl-substituted alkanes such as 2-methylhexane. The ionic liquids are preferably based on nitrogen-containing heterocycles or nitrogen-containing aliphatics as cations, and on inorganic anions such as haloaluminates. EP-A 5 403 236 does not contain any specific information as to the ratio in which the ionic liquid used as a catalyst is used relative to the paraffins to be isomerized.

In general, ionic liquids on the one hand and hydrocarbons (organic phases) on the other hand are immiscible or only of very limited miscibility; they form two separate phases. In order to be able to utilize this catalytic action, intensive contact has to be established between organic phase and the ionic liquid. For this purpose, the two phases are frequently mixed in stirred tanks with vigorous stirring to obtain dispersions. Depending on parameters such as the nature of the ionic liquid or of the organic phase or the phase ratio, the dispersion may either be in the form of a dispersion of an ionic liquid in the organic phase or may be a dispersion of the organic phase in the ionic liquid. Irrespective of the specific direction of dispersion present, it is a general problem in the case of such dispersions to remove the dispersed phase from the continuous phase after the reaction.

WO 2010/062922 discloses a multistage process for separating an ionic liquid from hydrocarbons using a coalescing filter. The characteristics of the coalescing filter material must be such that it has a stronger affinity for the ionic liquid than for the hydrocarbons. Suitable coalescing filter materials according to WO 2010/062922 are glass beads, stainless steel, glass fibers, polymer fibers or organic membranes, especially glass fibers. In the coalescing filter, separation of the ionic liquid from the hydrocarbons is accomplished.

It is an object of the present invention to provide a novel process for chemical conversion of at least one hydrocarbon in the presence of an ionic liquid, especially for isomerization of at least one hydrocarbon in the presence of an ionic liquid.

The object is achieved by a chemical conversion process for at least one hydrocarbon in the presence of an ionic liquid, which comprises performing the chemical conversion in a dispersion (D1), with dispersion of phase (B) in phase (A) in dispersion (D1), the volume ratio of phase (A) to phase (B) being in the range from 2.5 to 4:1 [vol/vol], phase (A) comprising greater than 50% by weight of at least one ionic liquid, and phase (B) comprising greater than 50% by weight of at least one hydrocarbon.

Figure 1:
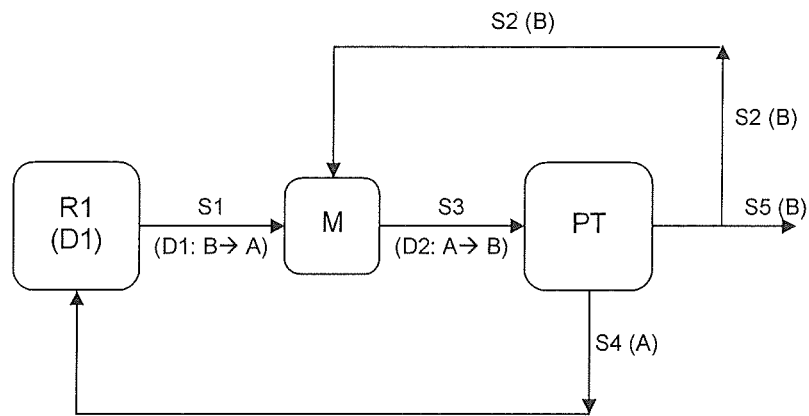
FIG. 1 illustrates the process according to the invention in a preferred embodiment.

Through the process according to the invention, it is advantageously possible to perform a chemical conversion, especially an isomerization, of hydrocarbons. Due to the specific volume ratio of phase (A) to phase (B) in the range from 2.5 to 4:1 [vol/vol], a higher space-time yield can be achieved. Due to this optimization, the apparatus complexity for performance of the process can also be reduced; for example, the apparatus in which the chemical conversion, especially the isomerization, is performed, can be kept small. It is thus possible to use smaller reactors, for example in the case of an isomerization the dimensions and/or number of stirred tanks used.

If, in the context of the present invention, after the chemical conversion, dispersion (D1) is used to invert the direction of dispersion (i.e. reversal of the direction of dispersion such that, after the inversion, phase (A) is dispersed in phase (B)), an additional advantage with regard to the removal of the ionic liquid from the hydrocarbons can be achieved, because the phase separation then proceeds more rapidly than in the converse case, which allows a reduction in the apparatus complexity for the phase separation.

The expression "inversion of the direction of dispersion" is defined in detail in the text which follows in connection with the introduction of stream (S2) comprising an excess of phase (B) into stream (S1) in the context of one embodiment of the process according to the invention.

If, in the context of the present invention, after the inversion of the direction of dispersion and the associated removal step in a phase separation unit, preferably in a phase separator, a further separation step is performed using a coalescing filter, especially a coalescing filter made from acrylic/phenolic resin or glass fiber, or using a downstream separator comprising a knit, improved removal of higher-viscosity components, especially ionic liquids, present in fine dispersion and/or in small amounts, is additionally found.

The chemical conversion process according to the invention, which is performed in a dispersion, for at least one hydrocarbon in the presence of an ionic liquid is defined in detail hereinafter.

The expression "chemical conversion process" or "chemical conversion" is understood in the context of the present invention, in principle, to mean any chemical conversion or chemical reaction which is known to those skilled in the art and in which at least one hydrocarbon is chemically converted, modified or altered in terms of its composition or structure in some other way.

The chemical conversion process is preferably selected from an alkylation, a polymerization, a dimerization, an oligomerization, an acylation, a metathesis, a polymerization or copolymerization, an isomerization, a carbonylation or combinations thereof. Alkylations, isomerizations, polymerizations etc. are known to those skilled in the art. Especially preferably in the context of the present invention, the chemical conversion process is an isomerization.

In the context of the present invention, phase (A) comprises at least one ionic liquid, the proportion of ionic liquid in phase (A) being greater than 50% by weight (based on the sum of all components of phase (A)). Phase (A) is preferably a phase which comprises ionic liquids and is immiscible or only of very limited miscibility with hydrocarbons and/or comprises not more than 10% by weight of hydrocarbons.

For example, phase (A) may comprise mixtures of two or more ionic liquids; phase (A) preferably comprises one ionic liquid. As well as the ionic liquid, phase (A) may also comprise further components miscible with the ionic liquid. Such components may, for example, by cocatalysts which are used in isomerization reactions using ionic liquids. A preferred example of such cocatalysts is hydrogen halides, especially hydrogen chloride. In addition, phase (A) may also comprise constituents or decomposition products of the ionic liquids which can form, for example, during the isomerization process, such as aluminum chloride. Preferably, in phase (A), the proportion of ionic liquid is greater than 80% by weight (based on the sum of all components of phase (A)).

Suitable ionic liquids in the context of the present invention are in principle all ionic liquids known to those skilled in the art, provided that they themselves catalyze the reaction performed in each case or have dissolution capacity for the catalyst used in each case. An overview with regard to suitable ionic liquids for the case of isomerization can be found, for example, in WO 2011/069929. In the context of the present invention, preference is given to an acidic ionic liquid. The ionic liquid present in phase (A) is preferably an ionic liquid, especially an acidic ionic liquid, having the composition $K1Al_nX_{(3n+1)}$ where K1 is a monovalent cation, X is halogen and $1<n<2.5$. K1 is preferably an unsubstituted or at least partly alkylated ammonium ion or a heterocyclic (monovalent) cation, especially a pyridinium ion, an imidazolium ion, a pyridazinium ion, a pyrazolium ion, an imidazolinium ion, a thiazolium ion, a triazolium ion, a pyrrolidinium ion, an imidazolidinium ion or a phosphonium ion. X is preferably chlorine or bromine.

The ionic liquid, especially the acidic ionic liquid, more preferably comprises, as a cation, an at least partly alkylated ammonium ion or a heterocyclic cation and/or, as an anion, a chloroaluminate ion having the composition $Al_nCl_{(3n+1)}$ where $1<n<2.5$. The at least partly alkylated ammonium ion preferably comprises one, two or three alkyl radicals (each) having 1 to 10 carbon atoms. If two or three alkyl substituents are present with the corresponding ammonium ions, the respective chain length can be selected independently; preferably, all alkyl substituents have the same chain length. Particular preference is given to trialkylated ammonium ions having a chain length of 1 to 3 carbon atoms. The heterocyclic cation is preferably an imidazolium ion or a pyridinium ion.

The ionic liquid, especially the acidic ionic liquid, especially preferably comprises, as a cation, an at least partly alkylated ammonium ion and, as an anion, a chloroaluminate ion having the composition $Al_nCl_{(3n+1)}$ where $1<n<2.5$. Examples of such particularly preferred ionic liquids are trimethylammonium chloroaluminate and triethylammonium chloroaluminate.

In the context of the present invention, a characteristic feature of phase (B) is that it comprises at least one hydrocarbon, the content of hydrocarbon in phase (B) being greater than 50% by weight (based on the sum of all components of phase (B)). Phase (B) is preferably a hydrocarbonaceous phase which is immiscible or has only very low miscibility with ionic liquids and/or which comprises not more than 1% by weight of ionic liquids (based on the total weight of the phase).

The specific composition of phase (B) depends on the chemical conversion process selected. At the start of a chemical conversion process, phase (B) has a different composition than after the corresponding chemical conversion process has ended. In other words, this means that phase (B) changes its composition due to the performance of the respective chemical conversion process. In principle, any desired hydrocarbons may be present in phase (B). The person skilled in the art knows on the basis of his or her general specialist knowledge which hydrocarbons are the best suited for which specific chemical conversion process, and in which compositions. Optionally, phase (B) may also comprise compounds which are not themselves hydrocarbons but are miscible therewith. The text which follows illustrates the composition of phase (B) with reference to the isomerization which is the preferred chemical conversion in the context of the present invention.

The hydrocarbon present in phase (B) prior to the chemical conversion, especially prior to the isomerization, is preferably methylcyclopentane (MCP) or a mixture of methylcyclopentane (MCP) with at least one further hydrocarbon selected from cyclohexane, n-hexane, isohexanes, n-heptane, isoheptanes and dimethylcyclopentanes.

Phase (B) prior to the chemical conversion, especially prior to the isomerization, more preferably comprises a mixture of methylcyclopentane (MCP) with at least one further hydrocarbon selected from cyclohexane, n-hexane, isohexanes, n-heptane, isoheptanes and dimethylcyclopentanes, the MCP/cyclohexane concentration ratio being preferably at least 0.2.

Particular preference is given in the context of the present invention to isomerizing methylcyclopentane (MCP) to cyclohexane.

The hydrocarbon present in phase (B) after the chemical conversion, especially after the isomerization, is preferably cyclohexane or a mixture of cyclohexane with at least one further hydrocarbon selected from methylcyclopentane (MCP), n-hexane, isohexane, n-heptane, isoheptane and dimethylcyclopentane.

Phase (B) after the chemical conversion, especially after the isomerization, especially preferably comprises a mixture of cyclohexane, MCP and at least one further hydrocarbon. The further hydrocarbon is preferably selected from n-hexane, isohexane, n-heptane, isoheptane and dimethylcyclopentane. More particularly, the proportion of branched hydrocarbons in the mixture (after the isomerization) is less than 5% by weight (based on the sum of all components of phase (B)). In addition, it is preferable in the process according to the invention that, after the isomerization, a smaller proportion of MCP and open-chain linear hydrocarbons is present in the resulting mixture present in phase (B) compared to the corresponding composition of phase (B) prior to the isomerization.

In the context of the present invention, the chemical conversion, especially the isomerization, is effected in a dispersion (D1) in which phase (B) is dispersed in phase (A). The direction of dispersion (i.e. the information as to which phase is in disperse form in the respective other phase) can be determined by examining a sample, optionally after addition of a dye which selectively stains one phase, under a transmitted light microscope. Phases (A) and (B) are each as defined above.

Dispersion (D1) can be produced by the method known to those skilled in the art; for example, such a dispersion can be obtained by vigorous stirring of the phases. In dispersion (D1), the volume ratio of phase (A) to phase (B) is in the range from 2.5 to 4:1 [vol/vol], preferably in the range from 2.5 to 3:1 [vol/vol].

The text which follows details further and/or preferred embodiments of the present invention, which are optionally illustrated with reference to the isomerization which is preferred for a chemical conversion process. All embodiments of the present invention which follow can also be used for other chemical conversion processes (than an isomerization).

The isomerization (chemical conversion) is preferably performed in a reaction apparatus or a cascade of reaction apparatuses; more particularly, it is effected in a stirred tank or a stirred tank cascade.

It is additionally preferable that dispersion (D1) additionally comprises a hydrogen halide and/or a gaseous hydrogen halide is contacted with dispersion (D1), the hydrogen halide preferably being HCl. D1 especially preferably additionally comprises HCl and/or gaseous HCl is introduced into dispersion (D1).

In addition, a stream (S1) may be discharged from the apparatus in which the chemical conversion is performed, in which case stream (S1) comprises at least a portion of the dispersion (D1) in which phase (B) is dispersed in phase (A), and phase (B) comprises at least one hydrocarbon which has been prepared in the chemical conversion. For the sake of completeness, it is pointed out that, in stream (S1), dispersion (D1) has the same chemical composition (including the ratios) as in the apparatus in which the chemical conversion is performed, if the chemical conversion is performed continuously. Stream (S1) in turn is preferably introduced into a phase separation unit. Phase separation units as such are known to those skilled in the art. This phase separation unit is preferably a phase separator.

In the phase separation unit, a stream (S4) comprising at least 70% by weight, preferably at least 90% by weight, of phase (A), and a stream (S5) comprising at least 70% by weight, preferably at least 90% by weight, of phase (B), can preferably be separated from one another. It is additionally preferred that stream (S4) is recycled into the apparatus in which the chemical conversion, preferably the isomerization, is performed. The above figures in % by weight are based on the corresponding amounts present in stream (S1).

In a further preferred embodiment, a stream (S2) comprising at least 70% by weight, preferably at least 90% by weight, of phase (B) is introduced into stream (S1). The above figures in % by weight are based on the total weight of stream (S2). This forms a stream (S3) comprising a dispersion (D2) in which phase (A) is dispersed in phase (B), i.e. the direction of dispersion is inverted. This stream (S3) in turn is introduced into the above-described phase separation unit rather than stream (S1). Optionally, stream (S2) can also be recycled directly into the phase separation unit or at another point in the process. Preferably, stream (S2) is introduced into stream (S1) in a stirred vessel or static mixer in which stream (S3) is formed.

It is additionally preferred that stream (S2) is branched off from stream (S5) obtained from the phase separation unit and optionally recycled into stream (S1) upstream of or into the phase separation unit.

In general, between 50 and 90% of the total amount of stream (S5) is removed as stream (S2) and recycled into stream (S1). However, it is also conceivable that, at least temporarily, larger amounts are recycled, or stream (S5) is even recycled completely.

FIG. 1 once again illustrates the process according to the invention in a preferred embodiment. In this embodiment, which is preferably performed as an isomerization, the chemical conversion is effected in reaction apparatuses or a cascade of reaction apparatuses (R1), for example stirred tanks. From (R1), stream (S1) comprising dispersion (D1), is combined in a mixing apparatus (M) with the recycled stream (S2) to form dispersion (D2). Stream (S3) is in turn introduced into a phase separation unit (PT), especially into a phase separator. For better understanding, FIG. 1 states the main components present in each of the streams in brackets below each of them. For streams (S1) and (S3), the respective expression in brackets also includes the direction of dispersion of the respective dispersions, the arrow expressing the direction of dispersion. This means that, for example, dispersion (D1) present in stream (S1) has a phase (B) dispersed in phase (A).

In a further preferred embodiment of the present invention, stream (S5) which, as described above, is obtained in a phase separation unit is used to perform (at least) one further phase separation step. This further phase separation step is preferably performed in order to remove residual amounts of phase (A) present in stream (S5). Especially preferably, after performance of this further phase separation step, only a small amount of phase (A), if any, is present in stream (S5) (<50 ppm by weight). This further phase separation step may directly follow the first phase separation step or may follow only after the removal of stream (S2) according to the variant described above. This further phase separation step preferably follows the removal of stream (S2).

Apparatuses for performance of this further phase separation step, called "downstream separators" hereinafter, are known to those skilled in the art. For this purpose, preference is given to using apparatuses suitable for removing residual amounts or smaller amounts (<2.5% by weight based on the total amount to be separated). Preferred apparatuses are coalescing filters or a downstream phase separator with or without internals. Possible internals are knits, random packings, structured packings or tubes.

This is preferably performed in such a way that removal of stream (S2) is followed by passing stream (S5) through the downstream separator described in the preceding paragraph, in order to remove residual amounts of phase (A) remaining in stream (S5). Especially preferably, after performance of this further phase separation step, only a small amount of phase (A), if any, is present in stream (S5) (<50 ppm by weight).

If a coalescing filter is used, this is preferably a coalescing filter made from glass fiber or acrylic/phenolic resin, especially of acrylic/phenolic resin. Coalescing filters made from acrylic/phenolic resin are commercially available, for example, from Fuhr GmbH (Germany) or from the manufacturer CUNO Fluid Purification. Such suitable coalescing filters (K) have finenesses of 1-150 μm, preferably 10, 25 or 50 μm, especially preferably 10 μm. In addition, 2 versions are possible with respect to the surface: grooved and ungrooved; ungrooved is preferred. The cartridges of the coalescing filter (K) as such have, for example, an internal diameter of 27 mm and an external diameter of 65 mm and are available in lengths of 4" to 60". The cartridge is preferably an asymmetric, resin-bonded filter cartridge with no support core. It preferably comprises essentially acrylic fibers bonded with phenol resin.

The coalescing filter can be integrated into a larger unit, for example a filter vessel. In the context of the present invention, a coalescing filter manufactured from glass fiber or acrylic/phenolic resin is preferably understood to mean the filter material as such. The other components of the filter unit, for example the vessel of the unit (filter vessel) or the filter module into which the filter material has been introduced may be manufactured from materials other than glass fiber and/or acrylic/phenolic resin. The expression "manufactured from" in the context of the present invention means that the material used for production of the filter material comprises glass fiber or acrylic/phenolic resin. The filter material preferably comprises at least 50% by weight, more preferably at least 75% by weight and especially at least 95% by weight of glass fiber or acrylic/phenolic resin.

If a downstream separator (also referred to as downstream phase separator) other than a coalescing filter is used, the downstream separator preferably comprises a knit, especially a glass fiber knit. Suitable knits, especially glass fiber knits, are known to those skilled in the art; they are commercially available, for example, from Rhodius (Germany). The preferred glass fiber knits are glass staple fibers having a fiber diameter between 0.1 and 0.6 mm, preferably between 0.14 and 0.3 mm. The knit comprises essentially wound (glass staple) fiber mats having a packing density between 100 and 800 kg/m$^3$, preferably 150 to 500 kg/m$^3$, more preferably 200 to 400 kg/m$^3$.

Optionally, the amount of phase (A) removed from the apparatus for performance of the further phase separation step can be recycled into the process according to the invention. Preference is given to recycling such a stream into the reaction apparatus or the cascade of reaction apparatuses in which the chemical conversion, preferably an isomerization, is performed in the presence of an ionic liquid. This recycle stream is preferably combined with stream (S4) which is obtained in the first phase separation unit. Optionally, these streams comprising phase (A) can also be recycled to another point in the process according to the invention, for example into a mixing or stirring apparatus, in order to control the concentration of phase (A) in dispersion (D2). It is also possible that a downstream separator is used without an upstream "first phase separation unit".

It is also possible that, after the residual amount of phase (A) has been removed from stream (S5) in the apparatus for performance of the further phase separation step, a further portion is removed, and this is optionally combined with stream (S2) and recycled into stream (S1).

In the context of the present invention, cyclohexane is preferably isolated from stream (S5). Processes and apparatuses for removal of cyclohexane from stream (S5), especially when it is a hydrocarbon mixture, are known to those skilled in the art. Optionally, prior to the removal of the cyclohexane, further purification steps (for example a wash with an aqueous and/or alkaline phase) can be conducted, these being known to those skilled in the art.

The invention is illustrated hereinafter by examples.

For the experiments, the following substances or compositions are used:

ionic liquid (A) having the composition $(CH_3)_3NH$ $Al_nCl_{3n+1}$ where n=1.82 according to elemental analysis.

Hydrocarbon mixture (B) having the composition
methylcyclopentane 20% by wt.
cyclohexane 50% by wt.
hexane 28%
isohexanes (technical grade mixture) 2% by wt.

Figure 2:
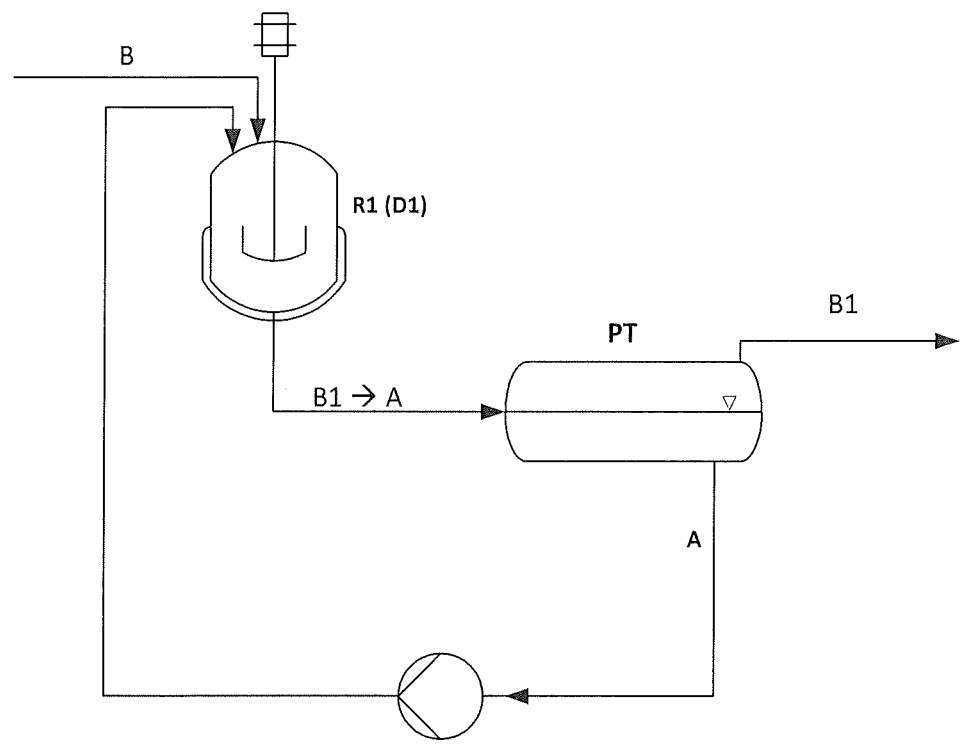
FIG. 2 illustrates the schematic of the test setup used in the examples.

The test setup used in the specific examples which follow is reproduced schematically in FIG. 2. In this context, the following generally applies:

The hydrocarbon mixture B (also referred to as phase (B) or organics) is introduced into a stirred tank in which a defined amount of ionic liquid is present. The conversion of the hydrocarbon mixture, an isomerization of methylcyclopentane to cyclohexane, takes place therein. In the course of this, the fill level of the reactor (R1) is regulated by adjustment of the variable overflow between R1 and PT. The dispersion of A and B is passed into a phase separator (PT) in which the two phases separate. The ionic liquid as the heavier phase is obtained here as the lower phase and is conveyed by a pump back into the vessel R1. The upper organic phase is drawn off and the composition thereof is analyzed by gas chromatography. In addition, gaseous HCl is used to establish a gauge pressure of 2 bar in the system.

EXAMPLE 1

Inventive Volume Ratio

The fill level of the reactor is set to 450 ml. The amount of ionic liquid in the system is selected such that a holdup of IL in the reactor of 360 ml is present. This gives rise to an organics volume of 90 ml. The dispersion (D1), in which phase (B) is now dispersed in phase (A), now has a volume ratio of 4 to 1 (phase (A) to phase (B)).

The feed of the hydrocarbon mixture is set to 150 g/h, at a reactor temperature of 50° C. After a run time of 92 hours, the output B1 (150 g/h) is analyzed by means of gas chromatography. The composition of phase B prior to isomerization and of B1 thereafter can be found in table 1.

TABLE 1

Composition of phase B before the reaction and of phase B1 after the reaction

| | Methylcyclo-pentane [wt. %] | Cyclohexane [wt. %] | Hexane [wt. %] | Isohexanes [wt. %] |
|---|---|---|---|---|
| Reactant measurement B | 20.08 | 50.31 | 27.91 | 1.7 |
| Product measurement B1 | 12.63 | 57.8 | 22.85 | 6.72 |

These measurement results and the experimental parameters give the following evaluation:

TABLE 2

Corresponding residence time, conversions, selectivity based on cyclohexane and the calculated rate constant of the isomerization

| | Residence time [h] | MCP conversion [%] | Hexane conversion [%] | Selectivity [CH] | k [1/h] |
|---|---|---|---|---|---|
| V(A)/V(B) = 4/1 | 1.661 | 36.7 | 18.13 | 100 | 4.18 |

The residence time k is calculated here as the quotient of IL volume divided by the organics feed. The constant k here is the calculated rate constant of the isomerization of methylcyclopentane to cyclohexane for a reactor with ideal backmixing, including reverse reaction.

COMPARATIVE EXAMPLE 2

Lower Volume Ratio

The fill level of the reactor is set to 450 ml. The amount of ionic liquid in the system is selected such that a holdup of IL in the reactor of 225 ml is present. This gives rise to an organics volume of 225 ml. The dispersion (D1) now has a volume ratio of 1 to 1 (phase (A) to phase (B)).

The feed of the hydrocarbon mixture is set to 150 g/h, at a reactor temperature of 50° C. After a run time of 92 hours, the output B1 (150 g/h) is analyzed by means of gas chromatography.

TABLE 3

Composition of phase B before the reaction and of phase B1 after the reaction

| | Methylcyclopentane [wt. %] | Cyclohexane [wt. %] | Hexane [wt. %] | Isohexanes [wt. %] |
|---|---|---|---|---|
| Reactant measurement B | 20.25 | 50.31 | 27.74 | 1.7 |
| Product measurement B1 | 13.76 | 56.80 | 24.49 | 4.95 |

These measurement results and the experimental parameters give the following evaluation:

TABLE 4

Corresponding residence time, conversions, selectivity based on cyclohexane and the calculated rate constant of the isomerization

| | Residence time [h] | MCP conversion [%] | Hexane conversion [%] | Selectivity [CH] | k [1/h] |
|---|---|---|---|---|---|
| V(A)/V(B) = 1/1 | 1.038 | 32.05 | 11.70 | 100 | 2.77 |

The residence time k is calculated here as the quotient of IL volume divided by the organics feed. The constant k here is the calculated rate constant of the isomerization of methylcyclopentane to cyclohexane for a reactor with ideal backmixing, including reverse reaction.

Comparison of the values from tables 2 and 4 shows that a higher volume ratio (ionic liquid/organics=4:1) causes a higher methylcyclopentane conversion and hence has a better space-time yield (11.24 g/h of cyclohexane at high ratio vs. 9.7 g/h of cyclohexane at low ratio).

The invention claimed is:

1. A process for isomerization of methylcyclopentane to cyclohexane in the presence of an ionic liquid, which comprises performing the isomerization in a dispersion (D1), wherein the dispersion (D1) comprises a phase (B) dispersed in a phase (A), the volume ratio of phase (A) to phase (B) being in the range from 2.5:1 to 4:1, phase (A) comprising greater than 50% by weight of at least one ionic liquid and not more than 10% by weight of hydrocarbons, and phase (B) comprising greater than 50% by weight of at least one hydrocarbon and not more than 1% by weight of ionic liquids;

wherein the isomerization is conducted in an apparatus, wherein a stream (S1) is discharged from the apparatus, wherein the stream (S1) comprises at least a portion of the dispersion (D1) in which phase (B) is dispersed in phase (A), and phase (B) comprises at least one hydrocarbon which has been prepared in the isomerization, wherein the at least one hydrocarbon present in phase (B) prior to the isomerization consists of methylcyclopentane or a mixture of methylcyclopentane with at least one further hydrocarbon selected from the group consisting of cyclohexane, n-hexane, isohexanes, n-heptane, isoheptanes, and dimethylcyclopentanes;

wherein a stream (S2) comprising at least 70% by weight of phase (B) is introduced into the stream (S1) to form a stream (S3) comprising a dispersion (D2) in which phase (A) is dispersed in phase (B).

2. The process according to claim 1, wherein the at least one ionic liquid present in the phase (A) comprises, as a cation, an at least partly alkylated ammonium ion or a heterocyclic cation or, as an anion, a chloroaluminate ion having the composition $Al_nCl_{3n+1}$) where 1<n <2.5.

3. The process according to claim 1, wherein the dispersion (D1) additionally comprises HCl or wherein gaseous HCl is introduced into the dispersion (D1).

4. The process according to claim 1, wherein the isomerization is performed in a stirred tank or a stirred tank cascade.

5. The process according to claim 1, wherein the stream (S1) is introduced into a phase separator.

6. The process according to claim 5, wherein., in the phase separator, a stream (S4) comprising at least 70% by weight of phase (A), and a stream (S5) comprising at least 70% by weight of phase (B), are separated from one another.

7. The process according to claim 6, wherein the stream (S4) comprises at least 90% by weight of phase (A), or the stream (S5) comprises at least 90% by weight of phase (B).

8. The process according to claim 6, wherein the stream (S4) is recycled into the apparatus.

9. The process according to claim 1, wherein the stream (S2) comprises at least 90% by weight of phase (B).

10. The process according to claim 1, wherein the stream (S3) is introduced into a phase separation unit.

11. The process according to claim 6, wherein the stream (S2) is branched off from the stream (S5) and recycled into the stream (S1) upstream of or into a phase separation unit.

12. The process according to claim 6, wherein the at least one hydrocarbon which has been prepared in the isomerization is cyclohexane, which is isolated from the stream (S5).

13. The process according to claim 1, wherein the volume ratio of phase (A) to phase (B) is 4:1.

14. The process according to claim 1, wherein the dispersion (D1) consists of phase (A) and phase (B), wherein phase (A) consists of the at least one ionic liquid, optionally up to 10% by weight of hydrocarbons, and optionally further components miscible with the at least one ionic liquid selected from the group consisting of cocatalysts and decomposition products of the at least one ionic liquid; and wherein phase (B) consists of the at least one hydrocarbon, optionally no more than 1% by weight of the at least one ionic liquid, and optionally compounds which are not hydrocarbons which are miscible therewith; and wherein the at least one hydrocarbon in phase (B) after the isomerization is cyclohexane or cyclohexane with at least one further hydrocarbon selected from the group consisting of methylcyclopentane, n-hexane, isohexane, n-heptane, isoheptane, and dimethylcyclopentane.

15. A process for isomerization of methylcyclopentane to cyclohexane in the presence of an ionic liquid, which comprises performing the isomerization in a dispersion (D1), wherein the dispersion (D1) comprises a phase (B) dispersed in a phase (A), the volume ratio of phase (A) to phase (B) being 4:1, phase (A) comprising greater than 50% by weight of at least one ionic liquid and not more than 10% by weight of hydrocarbons, and phase (B) comprising greater than 50% by weight of at least one hydrocarbon;

wherein the isomerization is conducted in an apparatus, wherein a stream (S1) is discharged from the apparatus, wherein the stream (S1) comprises at least a portion of the dispersion (D1) in which phase (B) is dispersed in phase (A), and phase (B) comprises at least one hydrocarbon which has been prepared in the isomerization, wherein the at least one hydrocarbon present in phase (B) prior to the isomerization consists of methylcyclopentane or a mixture of methylcyclopentane with at least one further hydrocarbon selected from the group consisting of cyclohexane, n-hexane, isohexanes, n-heptane, isoheptanes, and dimethylcyclopentanes;

wherein a stream (S2) comprising at least 70% by weight of phase (B) is introduced into the stream (S1) to form a stream (S3) comprising a dispersion (D2) in which phase (A) is dispersed in phase (B); and wherein phase (B) comprises 20% by weight methylcyclopentane, 50% by weight of cyclohexane, 28% by weight of hexane, and 2% by weight of isohexanes, based on the total weight of phase (B).

16. The process according to claim 1, wherein the process is performed continuously.

* * * * *